US00PP25733P3

(12) United States Plant Patent

Lintott et al.

(10) Patent No.: US PP25,733 P3

(45) Date of Patent: Jul. 21, 2015

(54) *LEUCANTHEMUM* PLANT NAMED 'REAL GLORY'

(50) Latin Name: *Leucanthemum×superbum*
Varietal Denomination: Real Glory

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 121 days.

(21) Appl. No.: 13/986,637

(22) Filed: May 20, 2013

(65) Prior Publication Data

US 2014/0345015 P1 Nov. 20, 2014

(51) Int. Cl.
*A01H 5/02* (2006.01)

(52) U.S. Cl.
USPC ..... Plt./285

(58) Field of Classification Search
USPC ..... Plt./285
CPC ..... A01H 5/02
See application file for complete search history.

(56) References Cited

PUBLICATIONS

American Nurseryman Perennials for 2013 Dec. 2012, pp. P10-P11.*
Radjevic. From the Road Scenes from the Trials. Lawn & Garden Retailer Jul. 2012, pp. 48-49.*

* cited by examiner

*Primary Examiner* — June Hwu
(74) *Attorney, Agent, or Firm* — Barbara Campbell; Cochran Freund & Young LLC

(57) ABSTRACT

A new cultivar of *Leucanthemum* plant named 'Real Glory' that is distinguishable by tight clumping habit, mid-dark green foliage and reflexed inflorescences with cream-white ray florets surrounding and contrasting with yellow disc florets, is disclosed.

2 Drawing Sheets

Figure 1:
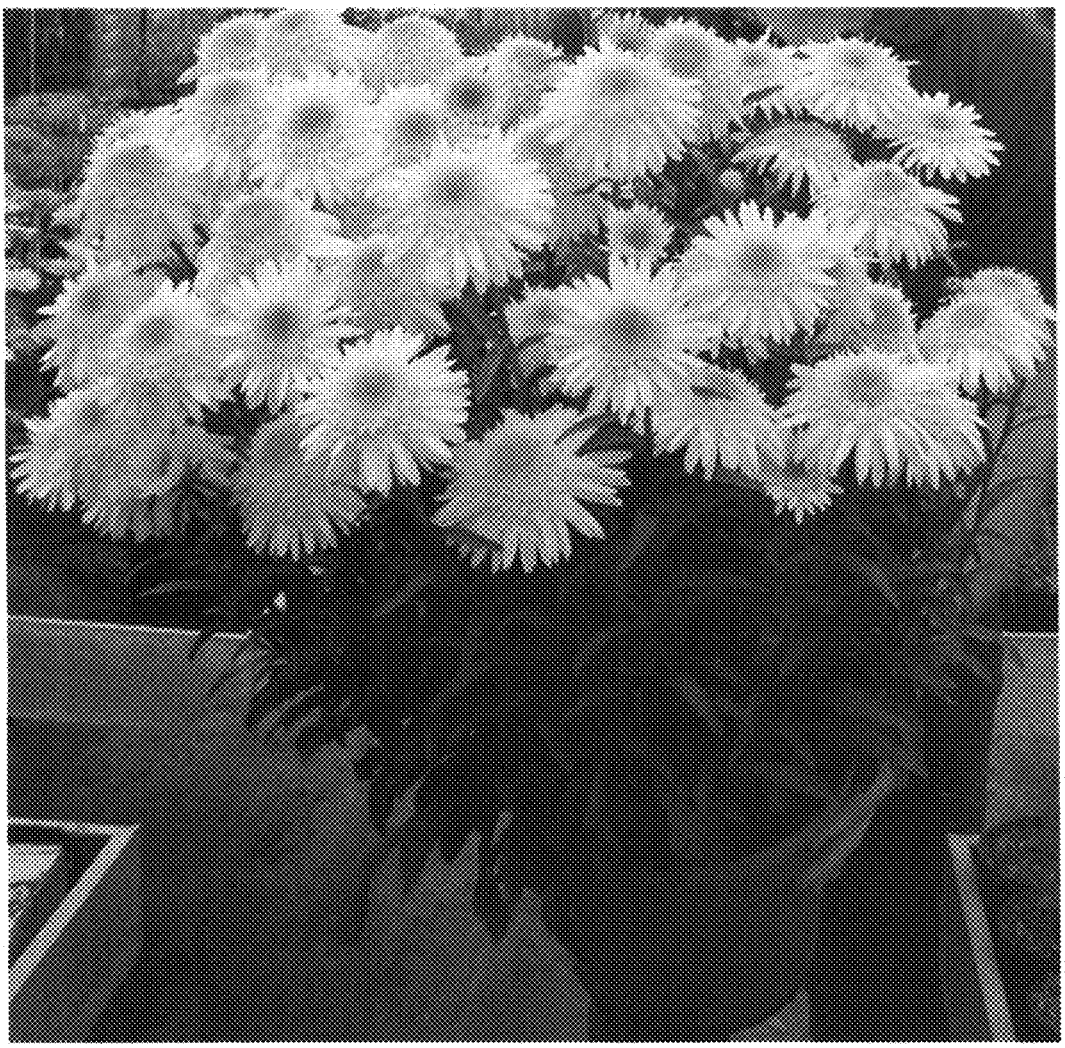

Genus and species: *Leucanthemum×superbum.*
Variety denomination: 'Real Glory'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum×superbum* and will be referred to hereinafter by the cultivar name 'Real Glory'. This application is co-pending with the application for the inventor's variety of *Leucanthemum* plant named 'Real Dream' (U.S. application Ser. No. 13/986,665).

*Leucanthemum* is a genus within the family Asteraceae in which the commonly referred to "flower" is botanically the inflorescence which is comprised of outer showy ray florets surrounding smaller disc florets.

'Real Glory' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Glory' is a seedling selection that resulted from the controlled pollination of a single plant of *Leucanthemum* 'Fiona Coghill' (unpatented) as the female parent, using pollen from a single plant of *Leucanthemum* 'Leumayel' (U.S. Plant Pat. No. 19,242) as the male parent. The inventors selected 'Real Glory' based on the criteria of vigor, reflexed ray florets and contrasting eye comprised of dense arrangement of yellow disc florets.

'Real Glory' was first asexually propagated by the inventors in West Sussex, United Kingdom in 2008 using the method of vegetative division and subsequently by basal shoot cuttings. Since that time under careful observation 'Real Glory' has been determined uniform, stable and true to type in subsequent generations of asexual propagation.

SUMMARY

The following traits have been repeatedly observed and represent the distinguishing characteristics of 'Real Glory'. In combination these traits set 'Real Glory' apart from all other existing varieties of *Leucanthemum* known to the inventor. 'Real Glory' has not been tested under all possible conditions and phenotypic differences may be observed with variations in environmental, climatic, and cultural conditions, however, without any variance in genotype.

1. 'Real Glory' exhibits tight clumping habit.
2. The foliage of 'Real Glory' is mid-dark green in color.
3. The inflorescence of 'Real Glory' is 8.5 cm in diameter and comprised of ray florets arranged around the central disc.
4. The ray florets of 'Real Glory' are cream-yellow in color.
5. The ray florets of 'Real Glory' develop initially in a flat horizontal plane but rapidly become markedly reflexed.

6. The flowers of 'Real Glory' are carried on a strong stiff stem and remain fresh in appearance for 10 to 14 days on the plant.
7. Flowering of 'Real Glory' commences in early summer and continues until fall.
8. After one year of growth in a 1 gallon container, a plant of 'Real Glory' is 60.0 cm in height and 40.0 cm in width.
9. 'Real Glory' prefers a rich moist well-drained medium.
10. 'Real Glory' is hardy in USDA Zone 5 (−20° F. or −28° C.).

COMPARISON WITH PARENTAL LINES AND KNOWN VARIETY

'Real Glory' is distinguishable from the female parent by the color of its ray florets and the prominence of the yellow eye. Whereas 'Fiona Coghill' exhibits cream-white ray florets, the ray florets of 'Real Glory' are cream-yellow in color. In addition, the inflorescence of 'Real Glory' is distinguished by a prominent yellow center comprised of yellow ray floret petal bases and yellow disc.

'Real Glory' is distinguishable from the male parent by inflorescence form. Whereas the inflorescence of 'Real Glory' consists of markedly reflexing ray florets, the ray florets of 'Leumayel' are arranged in a single layer.

The variety of *Leucanthemum* which the inventors consider to most closely resemble 'Real Glory' is the reflexed female parent variety 'Fiona Coghill'. Whereas 'Fiona Coghill' exhibits cream-white ray florets, the ray florets of 'Real Glory' are cream-yellow in color. In addition, the inflorescence of 'Real Glory' is distinguished by a prominent yellow center comprised of yellow ray floret petal bases and yellow disc.

BRIEF DESCRIPTION OF THE PHOTOGRAPHS

The accompanying color photographs illustrate the overall appearance of the new *Leucanthemum* cultivar named 'Real Glory' showing the color of foliage and flower as true as is reasonably possible to obtain in color reproductions of this type. Color in the photographs may differ from color values cited in the detailed botanical description, which accurately describe the actual color of 'Real Glory'. Both photographs were made using conventional techniques and although flower and foliage color may appear different from actual color due to light reflectance, it is as accurate as possible by conventional photography.

FIG. 1 illustrates an eighteen-month-old plant (from initial cuttings) which has been grown in a frost-free greenhouse in Gensingen, Germany. This photograph illustrates the robust habit of 'Real Glory' with stems and flowers held stiffly-erect. The illustrated plant has not been pinched or treated with any chemical growth regulators.

Figure 2:
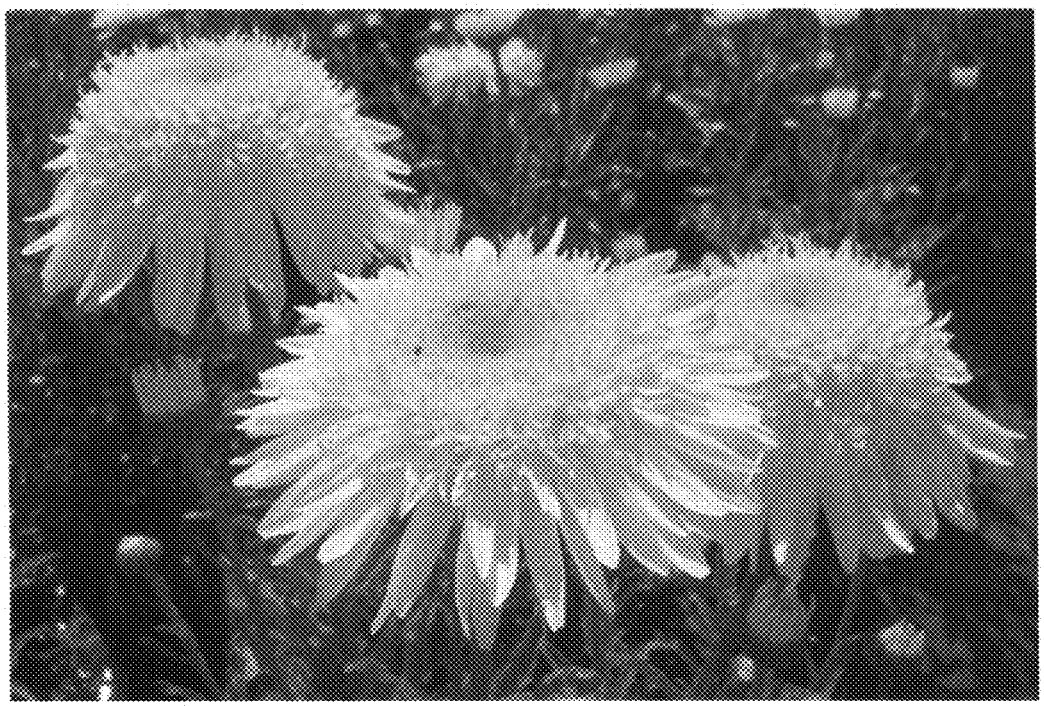

FIG. 2 depicts a close-up view of the flower on a 12-month-old plant of 'Real Glory' which was growing outdoors at the inventors' nursery in West Sussex, United Kingdom.

BOTANICAL DESCRIPTION OF THE PLANT

The following is a detailed botanical description of the new cultivar 'Real Glory'. Observations, measurements, values and comparisons were collected in Santa Barbara, Calif. during summer, from a 12-month-old plant growing outdoors in the garden border. Color determinations are made in accordance with The 2007 Royal Horticultural Society Colour Chart from London, England, except where general color terms of ordinary dictionary significance are used.

Botanical classification:

*Family*.—Asteraceae (formerly Compositae).
*Genus*.—*Leucanthemum*.
*Species*.—×*superbum*.
*Denomination*.—'Real Glory'.
*Common name*.—Shasta daisy.
*Habit*.—Tight clumping habit.
*Commercial category*.—Perennial herb.
*Use*.—For garden and landscape.
*Suggested commercial container size*.—4-inch and 1-liter containers.
*Parentage*.—*Leucanthemum*×*superbum* 'Real Glory' is a seedling selection resulting from the deliberate controlled cross-pollination of the following parents: Male parent: *Leucanthemum* 'Fiona Coghill' (unpatented). Female parent: *Leucanthemum* 'Leumayel' (U.S. Plant Pat. No. 19,242).
*Propagation method*.—Basal shoot cuttings and division.
*Rooting system*.—Fine and fibrous.
*Vigor*.—Vigorous.
*Time to develop roots* (*range*).—14 to 20 days are needed for an initial cutting to develop roots.
*Temperature to develop roots* (*range*).—The recommended air temperature is 20° C. to 21° C.
*Crop time* (*range*).—4 to 6 months to produce a 1-liter container from a basal shoot cutting.
*Plant dimensions* (*one year*).—60.0 cm in height and 40.0 cm in width.
*Cultural requirements*.—Grow in full sun and rich, moist moderately fertile well-draining soil.
*Pest or disease resistance*.—No disease or pest resistance known to the inventor.
*Hardiness*.—USDA Zone 5.

Stem:

*Branching*.—Basal.
*Color*.—RHS 145A.
*Basal stem length*.—15.0 cm.
*Diameter*.—1.0 cm.
*Shape*.—Cylindrical.
*Surface*.—Smooth, glabrous.

Foliage:

*Type*.—Evergreen.
*Arrangement* (*combination*).—Opposite and basal.
*Internode length* (*range*).—0.5 cm to 1.0 cm.
*Division*.—Simple.
*Margin*.—Coarsely irregularly dentate; teeth spaced at 2.0 cm to 3.0 cm, depth 3.0 mm to 8.0 mm.
*Apex*.—Acute.
*Base*.—Attenuate.
*Leaf attachment* (*range*).—Basal to sessile.
*Leaf color* (*abaxial surface*).—RHS N137B.
*Leaf color* (*adaxial surface*).—RHS 137D.
*Leaf shape*.—Lanceolate.
*Leaf dimensions* (*when fully expanded*).—28.0 cm in length, 4.5 cm in width.
*Leaf venation*.—Pinnate.
*Vein color* (*both surfaces*).—RHS 145A.
*Leaf surface* (*both surfaces*).—Glabrous.

Inflorescence:

*Inflorescence type*.—Anemone type capitulum.
*Inflorescence quantity* (*average*).—30 (including buds) per 2-liter container plant.

*Inflorescence diameter.*—8.5 cm.
*Inflorescence depth* (*includes ray florets when fully reflexed*).—6.0 cm.
*Inflorescence shape*.—Radiate when ray florets horizontal; globose when ray florets are reflexed.
*Inflorescence color*.—Central disc color: Ranges from RHS 7A to RHS 7B. Ray floret color: Ranges between RHS 155C and RHS NN155B.
*Fragrance*.—Musty, characteristic of wild oxeye daisy.
*Aspect*.—Disc facing upward.
*Blooming season*.—Early summer to fall.
*Lastingness of inflorescence* (*range*).—10 to 14 days on the plant; ray florets are persistent.

Bud:
*Bud dimensions.*—0.50 cm in height and 1.5 cm in diameter.
*Bud shape*.—Flattened sphere.
*Bud color*.—RHS 147B.
*Bud surface*.—Glabrous.

Peduncle:
*Peduncle shape*.—Cylindrical.
*Peduncle length.*—16.0 cm to 35.0 cm.
*Peduncle diameter.*—4.0 mm to 6.0 mm.
*Peduncle surface*.—Furrowed with sparse hairs.
*Peduncle color*.—RHS 144A.
*Peduncle strength*.—Stiff, strong.

Ray florets:
*Ray floret shape*.—Initially cymbiform, becoming flat when fully expanded; corolla tube appears to subtend single ligule or petal.
*Ray floret quantity.*—45 to 50 per inflorescence.
*Ray floret arrangement*.—Radiate.
*Ray floret aspect*.—Initially upright, opening to horizontal; maturing to reflex angle approximately 150° from the vertical.
*Ray floret corolla tube dimensions.*—5.0 mm in length, 1.0 mm in diameter.
*Ray floret corolla tube color*.—RHS 144C.

Petals:
*Petal shape*.—Strap-like.
*Petal surface* (*abaxial*).—Glabrous.
*Petal surface* (*adaxial*).—Pubescent.
*Petal apex*.—Predominantly truncate, occasionally rounded; emarginate.
*Petal margin*.—Entire.
*Petal dimensions* (*when ray floret is horizontal*).—3.0 cm in length and 7.5 mm in width.
*Petal dimensions* (*when ray floret is largest and fully reflexed*).—4.5 cm in length and 1.0 cm in width.
*Petal color* (*when ray floret is horizontal*).—RHS 155C except base RHS 144C.
*Petal color* (*when ray floret is largest and fully reflexed*).—RHS NN155B except base RHS 144C.

Involucral bract:
*Quantity* (*average*).—More than 40 per inflorescence, overlapping.
*Bract color* (*abaxial and adaxial surfaces*).—RHS 147B.
*Bract length.*—9.0 mm.
*Bract width.*—3.0 mm.
*Bract apex*.—Rounded.
*Bract base* (*range*).—Rounded to truncate.
*Bract surface* (*both surfaces*).—Glabrous.
*Bract shape*.—Lanceolate.
*Bract margin*.—Ciliate, fine hairs, color RHS 175A.

Disc floret:
*Disc diameter.*—3.0 cm.
*Disc floret quantity* (*average*).—Approximately 400 per inflorescence, massed at center of receptacle.
*Disc floret color*.—Ranges from RHS 7A to RHS 7B.
*Disc floret dimensions.*—7.0 mm in depth and 1.0 mm in diameter.
*Disc floret shape*.—Tubular.
*Disc floret petals*.—Ranges from 3 to 5 in number, basally fused.
*Disc floret petal* (*immature, prior to opening*).—4.0 mm in length, 1.0 mm in width, color RHS 7A.
*Disc floret petal* (*fully open*).—10.0 mm to 11.0 mm in length, 1.5 mm in width, furrowed, color RHS 7B except apex RHS 7A.
*Disc floret petal apex*.—Acute.
*Receptacle color*.—RHS 147B.
*Receptacle shape*.—Convex.
*Receptacle dimensions.*—0.5 cm in height and 2.5 cm in diameter.

Reproductive organs:
*Ray flowers*.—Androecium (stamens, anthers, filaments, and pollen): Absent. Pistil: 1.5 mm in length. Stigma: 1.0 mm in length, appears bifid, color is light brown. Ovary: Superior, globose, less than 1.0 mm in diameter and color is RHS 144D.
*Disc flowers*.—General: Stigma, style, and ovary not observed. Stamens: 5, probably fused appearing as 1; length is 1.0 mm and color is RHS 175A. Pollen: Low amount; color is close to RHS 15A (Yellow-Orange). Pistil: 1, less than 1.0 mm in length.

Seed: None observed to date.

We claim:

1. A new and distinct cultivar of *Leucanthemum* plant named 'Real Glory' as described and illustrated herein.

* * * * *